United States Patent
Reinelt

(10) Patent No.: US 9,636,240 B2
(45) Date of Patent: May 2, 2017

(54) METHOD FOR PRODUCING AN ADAPTED LINER AND LINER

(75) Inventor: Stefan Reinelt, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 368 days.

(21) Appl. No.: 12/921,326

(22) PCT Filed: Mar. 6, 2009

(86) PCT No.: PCT/DE2009/000308
§ 371 (c)(1),
(2), (4) Date: Sep. 7, 2010

(87) PCT Pub. No.: WO2009/109182
PCT Pub. Date: Sep. 11, 2009

(65) Prior Publication Data
US 2011/0004323 A1  Jan. 6, 2011

(30) Foreign Application Priority Data
Mar. 7, 2008  (DE) .................. 10 2008 013 527

(51) Int. Cl.
*A61F 2/78* (2006.01)
*A61F 2/50* (2006.01)

(52) U.S. Cl.
CPC .......... *A61F 2/7812* (2013.01); *A61F 2/5046* (2013.01); *A61F 2002/5052* (2013.01)

(58) Field of Classification Search
CPC .................. A61F 2/80; A61F 2/7812
USPC .......................................... 623/36
See application file for complete search history.

(56) References Cited

U.S. PATENT DOCUMENTS

| | | | |
|---|---|---|---|
| 3,732,578 A * | 5/1973 | Pollack ........................ | 623/36 |
| 5,387,245 A | 2/1995 | Fay et al. | |
| 5,507,834 A * | 4/1996 | Laghi ............................ | 623/36 |
| 5,571,208 A * | 11/1996 | Caspers ........................ | 623/32 |
| 5,888,231 A | 3/1999 | Sandvig et al. | |
| 6,136,039 A * | 10/2000 | Kristinsson ........... | A61F 2/7812 623/36 |
| 6,231,616 B1 * | 5/2001 | Helmy .......................... | 623/34 |
| 6,362,387 B1 * | 3/2002 | Carlson et al. ................. | 602/41 |
| 6,918,936 B2 | 7/2005 | Hellberg | |
| 7,144,429 B2 * | 12/2006 | Carstens ........................ | 623/34 |

(Continued)

FOREIGN PATENT DOCUMENTS

DE   1959638 U    5/1967
DE   19823753 A1  12/1999

(Continued)

OTHER PUBLICATIONS

PCT International Search Report for PCT/DE2009/000308, mailed Jul. 30, 2009.

*Primary Examiner* — Bruce E Snow
*Assistant Examiner* — Melissa Hoban
(74) *Attorney, Agent, or Firm* — Holland & Hart

(57) ABSTRACT

The invention relates to a method for producing an adapted liner for placement on a stump (1), particularly an amputation stump, comprising the following steps: selecting a prefabricated liner (3) as a function of the size of the stump; applying a filling compound (2) onto regions of the stump (1) that deviate from the inside contour of the prefabricated liner; and connecting the filling compound (2) to the prefabricated liner (3).

22 Claims, 1 Drawing Sheet

(56) References Cited

U.S. PATENT DOCUMENTS

Figure 1:
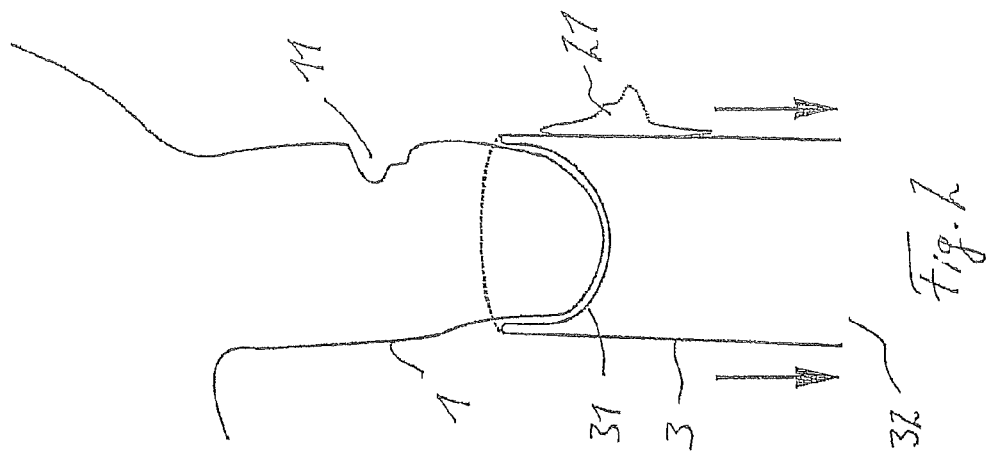

2005/0101693 A1   5/2005  Arbogast et al.
2006/0111792 A1*  5/2006  Shannon .................... 623/36
2006/0179935 A1*  8/2006  Warila ..................... A61F 2/76
                                                      73/172

FOREIGN PATENT DOCUMENTS

WO    9804218 A1   2/1998
WO    9945862 A1   9/1999

* cited by examiner

METHOD FOR PRODUCING AN ADAPTED LINER AND LINER

The invention relates to a method for producing an adapted liner and to a liner composed of a tubular main body.

In prosthetics, liners are provided as an intermediate element between the limb and the prosthesis. The liner forms an intimate connection with the stump, and it is also possible for the liner to be connected to the prosthesis via a mechanical lock. In addition, a vacuum ensures an improved adherence of the prosthesis to the liner, such that the patient provided with the liner has an improved prosthesis feel and improved security against accidental detachment of the prosthesis.

Such liners are generally produced from a silicone material. Alternatively, however, polyurethane or block copolymer materials can also be used. To be able to adapt the liners to the physiological conditions presented by the patient, an impression is taken of the stump on which the liner is to be placed, a positive model of the stump is produced from plaster or plastic, and the liner is individually prepared on the basis of the stump model. The individual preparation of a liner is highly complicated and therefore very expensive. Considerable costs are entailed in providing a patient with a liner that is produced in this way.

Furthermore, standard liners are available that are prefabricated in different sizes. Individual adaptation is not carried out and for this reason, despite the different sizes, standard liners may lead to hollow spaces and, consequently, to instability.

The object of the present invention is to make available a method for producing a liner and to make available a liner, with which the disadvantages of the prior art can be avoided. According to the invention, this object is achieved by a method having the features of claim 1 and by a liner having the features of claim 12. Advantageous embodiments and developments of the invention are described in the dependent claims.

In the method according to the invention for producing an adapted liner for placement on a stump, particularly an amputation stump, a prefabricated liner, a so-called standard liner, is firstly selected as a function of the size of the stump. A prefabricated liner is produced by the usual method steps that are known from the prior art. The prefabricated liner is composed mainly of an elastomer, for example silicone, polyurethane or a copolymer and, if appropriate, is laminated on the outside or provided with a reinforcing insert. After the prefabricated liner has been selected, a filling compound is applied to regions of the stump that deviate from the inside contour of the prefabricated liner. The standard liners generally have a structure that is symmetrical in rotation and have a closed end, resulting overall in a cylinder shape or a parabolic shape. If the stump has shapes deviating from the normal round inner contour, these shapes are compensated using a filling compound. After the filling compound has been applied in or on the regions of the stump that deviate from the inside contour of the prefabricated liner, the filling compound comes into contact with the inner face of the prefabricated liner and connects to the prefabricated liner, thus resulting in a personalized liner. The connection of the filling compound to the prefabricated liner is preferably effected via a mechanical, physical connection of the filling compound to the liner. The liner and the filling compound form an intimate and firm connection. A chemical crosslinking between the filling compound and the liner does not take place insofar as the liner has fully reacted. Primers increase the adherence without causing transboundary chemical crosslinking. Alternatively, a cohesive connection between the prefabricated liner and the filling compound can take place if the materials used, generally elastomers, so permit.

In a variant of the invention, the filling compound is firstly applied to the stump, preferably in the regions where constrictions, depressions or the like are present and where deviations from the inside contour of the prefabricated liner are to be expected. The prefabricated liner is then placed, particularly rolled on, over the stump with the applied filling compound, such that the inner face of the liner comes into contact with the filling compound. After placement of the standard liner, the filling compound and the prefabricated liner are connected to each other, thus resulting in an individualized liner that has been produced in a simple manner on the basis of the prefabricated standard liner. The advantage of this variant is that it is easy to implement and does not require any special tools, and the filling compound spreads out automatically when the prefabricated liner is placed onto or rolled onto the stump. The pressure exerted by the prefabricated liner distributes the filling compound in such a way that the differences between the stump contour and the inner contour of the prefabricated liner are compensated.

Alternatively, the prefabricated liner is placed in position and the filling compound is then applied through the prefabricated liner to the regions that are to be filled. The advantage of this variant is that, after the placement of the prefabricated liner, the generally transparent or translucent material of the liner makes it possible to see where the prefabricated liner does not bear fully on the stump, in other words where free spaces form between the stump and the inside contour of the prefabricated liner. The filling compound is introduced into these free spaces, for example through the wall of the prefabricated liner by means of a syringe or the like, or from the direction of the open, proximal end of the liner, e.g. via a needle or a tube. The advantage of this variant is that it is possible to see where free spaces have to be filled when individualizing the prefabricated liner, with the result that it is possible to monitor very exactly how much filling compound is introduced and where.

The filling compound is applied particularly in the region of scar contractions, oblique stump planes, dysmelias, amelias or concavities, so as to obtain an approximately symmetrical outer contour of the stump provided with the filling compound.

The prefabricated liner is preferably in the form of a silicone liner, and the filling compound in the form of an uncrosslinked silicone rubber, in order to provide, in addition to the elastic properties of the silicone rubber, also a high degree of skin compatibility and adherence. Moreover, other elastomer materials, for example polyurethane or copolymers, can also be used as liner materials. These materials can also be used as materials for the filling compound, such that the finished, individualized liner is made substantially of one material.

Since the adapted, individualized liner with the inwardly extending projections resulting from the crosslinked filling compound connected to the standard liner is not designed to remain adhering to the skin surface, the skin surface is isolated before the filling compound is applied, for example by applying plaster cast insulating cream or Vaseline, particularly in order to ensure that any hairs present on the stump do not remain fixed to the filling compound. If no hairs are present and if there are no sensitive areas on the stump, it is possible to do without prior insulating.

A preferred way of applying the liner to the stump involves the prefabricated liner being turned inside out, such that the inner face of the liner located underneath during use is positioned as an outwardly curved cap in front of the stump end. The liner is then rolled onto the stump from the direction of the stump end, such that the filling compound is forced upward. This way of rolling and applying the liner onto the stump ensures that no air is included, with the result that no undesired hollow spaces form. This method of placement can also be used when the filling compound is introduced only after placement.

In order to facilitate a connection of the filling compound to the inner face of the liner, the inner face of the prefabricated liner is degreased before placement, such that the freedom from grease ensures a good connection of the filling compound to the material of the liner, preferably the silicone.

In a development of the invention, the initially uncrosslinked filling compound is quickly applied to the skin surface, for example from a pistol, and the liner is directly thereafter rolled over the still uncrosslinked filling compound such that the still uncrosslinked filling compound connects cohesively to the prefabricated liner. This connection can take place through vulcanization of the filling compound in the applied state, with the filling compound then connecting cohesively to the prefabricated liner.

Following the connection of the filling compound to the prefabricated liner, the liner is removed and any burrs present are smoothed off in order to make the adapted liner more comfortable to wear. If re-shaping work is needed, filling compound is applied again to the stump, and the already partially adapted liner is then adapted fully to the stump, by means of the only partially adapted liner being placed on the stump again and being connected to the filling compound such that free spaces that still remained after the first adaptation are filled. The two variants described above can be combined such that, in the first run, the filling compound is applied to the stump before the placement of the prefabricated liner, and the liner is then placed in position. Should it then be found that free spaces are still present, these can be filled by more filling compound being introduced through the liner or from the direction of the proximal opening. This introduction through the liner can also take place before the detachment of the liner after connection to the previously applied filling compound. After the application of the filling compound and the subsequent placement of the prefabricated liner, it is possible to check whether there are still any free spaces between the liner and the stump surfaces; these free spaces can then be filled with the filling compound directly through the liner. It is also possible that the prefabricated liner is first placed in position, filling compound is introduced and, after removal of the liner from the stump, filling compound is applied to the stump surface, and the already partially individualized liner is placed in position, e.g. rolled onto the stump.

The liner is composed of a tubular main body which is open at one end and closed at the opposite end. The main body is preferably a prefabricated standard liner. At least one shaped body is formed on the inner face of the main body subsequently, i.e. after production of said main body, which shaped body at least partially fills a free space between the main body and the stump, said shaped body being secured cohesively on the main body. Whereas, in the case of conventional individual liners, an impression of a previously prepared cast or model is made and the liners are generally produced in an immersion method, it is possible, with the liner according to the invention, to use a conventional standard liner and individualize it in such a way that it is adapted to the specific shape of the stump or limb. The free spaces are the deviations between the inner contour of the main body or standard liner and the outer contour of the stump.

The main body can also be pre-flexed in order to achieve a better fit in the joint region, since it better follows the anatomical conditions.

The main body and the at least one shaped body are preferably made from silicone rubber, in which case the cohesive securing of the shaped body to the main body can take place through vulcanization. Likewise, the main body and the filling compound can be produced from another elastomer material, for example a copolymer or a polyurethane material.

Figure 2:
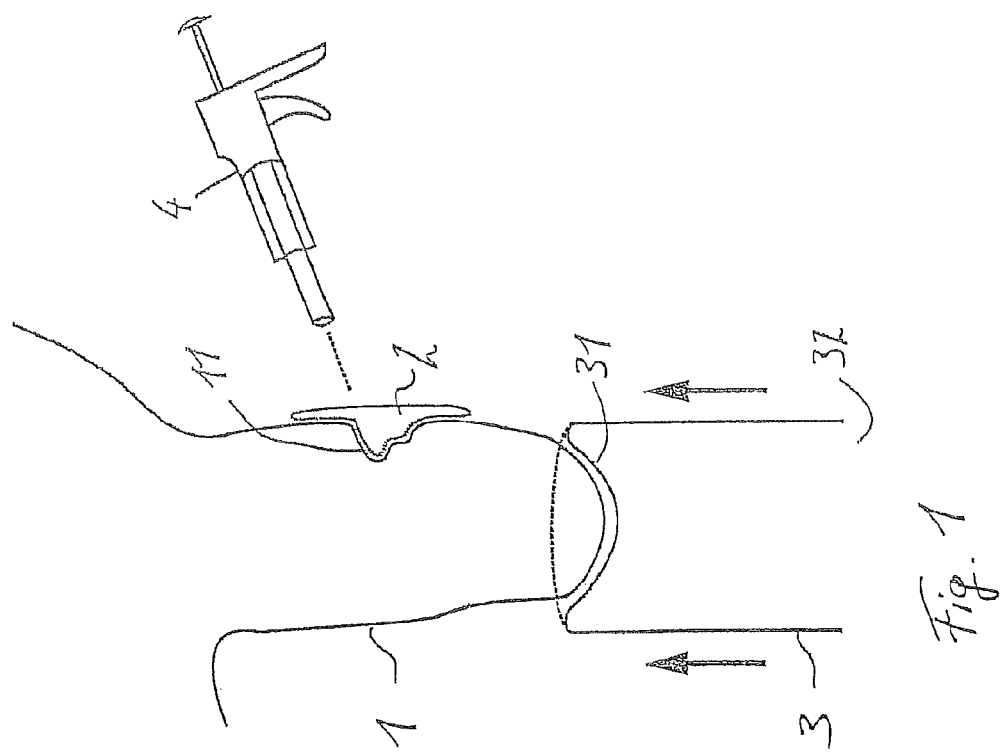

An illustrative embodiment of the invention is explained in more detail below with reference to the attached figures, where FIG. 1 shows a stump and a liner after a filling compound has been applied; and FIG. 2 shows a fully adapted liner after removal from the stump.

An amputation stump 1 of a limb is shown in FIG. 1. The outer shape of the stump 1 has irregularities 11, which can have various causes. In addition to the natural asymmetry of a limb and the natural deviation from an ideal smooth shape, the irregularities can be the result of abnormalities, such as dysmelias or amelias, or of injuries or surgical scars. This is shown schematically in FIG. 1 on the basis of a scar contraction 11.

FIG. 1 also shows a prepared, prefabricated standard liner 3, the actual inner face of which is turned outward. The standard liner 3 is tubular and has a closed end 31 and an opposite open end 32. In the starting position, which is indicated by the broken line, there is a slight outward curvature. The closed end 31 is placed onto the distal end of the stump 1 in such a way that the closed end 31 bears fully and smoothly on the stump 1.

If the standard liner 3 were then to be pulled further up the stump 1 in the direction of the arrows in FIG. 1, the scar contraction 11 would not come into contact with the inner face of the liner, such that a hollow space would be present between the inner face of the liner and the surface of the stump, and this would mean the wearing comfort and secure fit of the prosthesis (not shown) that is then to be applied.

For this reason, a filling compound 2 is first applied from a static mixer 4 into the scar contraction 11, which serves as an example of an irregular shape of the stump surface. The amount of filling compound 2 is such that the irregularity 11 is completely compensated. If appropriate, an excess amount can be applied and then spread across the surrounding stump 1. The application is carried out as far as possible without bubbles and speedily, such that the uncrosslinked filling compound 2 cannot crosslink with one another. Then, directly after the application, the liner 3 serving as the main body is rolled over the still unvulcanized filling compound 2 within the irregularity 11 and over the stump 1. This is done in the direction of the two arrows in FIG. 1. By rolling the liner 3 from the distal end of the stump 1 to the proximal end, and by means of the tight bearing of the liner 3 on the stump 1, it is possible to place the liner 3 onto the stump 1 without air inclusions. A possible excess amount of the filling compound 2 is forced upward and can be scraped off with a spatula. By virtue of the compression of the liner 3 on the stump 1 and on the filling compound 2, the filling compound 2 automatically shapes itself with a form fit to the hollow spaces, oblique planes, dysmelias, amelias or scar contractions 11 and at the same time bears on the liner 3.

After the waiting period required by the material, the uncrosslinked silicone rubber compound has vulcanized and connected to the inner face of the liner 3. The filling compound 2 is preferably made from an uncrosslinked silicone rubber material which vulcanizes within a short period of time and connects to the main body 3, likewise produced from a silicone rubber material.

Following the cohesive connection of the filling compound 2 to the main body 3, the now adapted standard liner 3 is withdrawn from the stump 1, by means of the proximal open end of the liner 3 being pulled off in the direction of the distal end, in the direction of the arrows in FIG. 2. In doing this, the inner face of the liner 3 is turned outward. A shaped body 21 corresponding exactly to the recess or irregularity 11 in the stump 1 is then formed on the liner 3. The shaped body 21 can then be worked, for example ground with a funnel scourer, in order to break any sharp edges that may be present and in order to smooth the surface and transitions. Should it be necessary to apply a filling compound 2 a second time, this can be done in the same way as described above. Using this technique, it is possible to compensate for volume differences between a main body 3 of the liner and a stump 1 without having to prepare an individual impression of the stump 1. Similarly, it is not necessary to mold a prosthesis socket thermoplastically onto the stump 1 or to adhesively fix separate pads to the prosthesis socket or to the stump 1.

Surprisingly, the filling compound made from an uncrosslinked silicone rubber has been found to connect to the already vulcanized silicone materials of the prefabricated liner. The use of adhesion promoters is useful here, but not absolutely necessary. As adhesion promoters it is possible to use silicones that crosslink at room temperature and that are present in a two-component formulation and can be applied directly before placement of the prefabricated liner. Silicones crosslinked at high temperature and also silicones crosslinked at low temperature can be used as liner material. In addition to silicones that crosslink at room temperature, the use of silicones crosslinking at high temperature is also possible, in which case the silicones crosslinking at high temperature begin to vulcanize at a temperature above 100° C.

In addition to silicones, it is also possible to use other elastomers such as polyurethane or copolymers as materials for the filling compound or the main body. In addition to the method described with reference to the figures, the filling compound can also be introduced through the main body, that is to say through a hole in the wall of the main body, and distributed between the main body and the stump.

The invention claimed is:

1. A method for producing an adapted liner for placement on an amputation stump, the method comprising:
    selecting a flexible prefabricated liner as a function of the size of the stump;
    applying an uncrosslinked filling compound directly to a surface of the stump at regions of the stump that deviate from an inside contour of the prefabricated liner;
    positioning the prefabricated liner on the stump, the uncrosslinked filling compound spreading out as the prefabricated liner is positioned on the stump;
    connecting the uncrosslinked filling compound to an inner surface of the prefabricated liner by vulcanizing the uncrosslinked filling compound into a crosslinked filling compound while the prefabricated liner is positioned on the stump, the connected crosslinked filling compound and prefabricated liner forming an at least partially adapted liner.

2. The method as claimed in claim 1, wherein the prefabricated liner is placed onto the stump after the uncrosslinked filling compound has been applied.

3. The method as claimed in claim 1, wherein the uncrosslinked filling compound is applied to the stump in the region of scar contractions, oblique stump planes, dysmelias, amelias or concavities.

4. The method as claimed in claim 1, wherein the prefabricated liner is made from a silicone material, polyurethane material or copolymer material, and the uncrosslinked filling compound is made from uncrosslinked silicone rubber, polyurethane or copolymer material.

5. The method as claimed in claim 1, wherein a skin surface of the stump is isolated before the uncrosslinked filling compound is applied.

6. The method as claimed in claim 1, wherein the prefabricated liner, with the inner face turned outward, is rolled onto the stump from the direction of the stump end.

7. The method as claimed in claim 1, wherein the inner face of the prefabricated liner is degreased before placement.

8. The method as claimed in claim 1, wherein the uncrosslinked filling compound connects cohesively to the prefabricated liner.

9. The method as claimed in claim 1, wherein, after connecting the uncrosslinked filling compound to the prefabricated liner, the at least partially adapted liner is removed and mechanically worked.

10. The method as claimed in claim 1, further comprising applying additional uncrosslinked filling compound to the at least partially adapted liner and connecting the additional uncrosslinked filling compound to the at least partially adapted liner.

11. The method as claimed in claim 1, wherein the uncrosslinked filling compound adheres to the stump.

12. The method as claimed in claim 1, wherein the at least partially adapted liner is insertable into a socket of a prosthetic device while mounted to the stump.

13. The method as claimed in claim 1, wherein the prefabricated liner and the uncrosslinked filling compound comprise the same material.

14. A method for producing an adapted liner for placement on an amputation stump, the method comprising:
    applying an uncrosslinked filling compound directly to a surface of the stump;
    mounting a flexible prefabricated liner to the stump, the uncrosslinked filling compound being applied to the stump independent of mounting the prefabricated liner to the stump, the uncrosslinked filling compound spreading out as the liner is positioned on the stump;
    connecting the uncrosslinked filling compound to an inner surface of the prefabricated liner by vulcanizing the uncrosslinked filling compound into a crosslinked filling compound while the prefabricated liner is positioned on the stump, the connected crosslinked filling compound and prefabricated liner forming an at least partially adapted liner.

15. The method as claimed in claim 14, wherein the uncrosslinked filling compound is applied to the stump in the region of scar contractions, oblique stump planes, dysmelias, amelias or concavities of the stump.

16. The method as claimed in claim 14, wherein the prefabricated liner comprises silicone material, polyurethane material or copolymer material, and the uncrosslinked filling compound comprises uncrosslinked silicone rubber, polyurethane or copolymer material.

17. The method as claimed in claim 14, further comprising isolating a skin surface of the stump before the uncrosslinked filling compound is applied.

18. The method as claimed in claim 14, further comprising rolling the prefabricated liner, with the inner face turned outward, onto the stump from the direction of the stump end.

19. The method as claimed in claim 14, further comprising degreasing the inner face of the prefabricated liner before mounting.

20. The method as claimed in claim 14, wherein the uncrosslinked filling compound connects cohesively to the prefabricated liner.

21. The method as claimed in claim 14, further comprising removing and mechanically working the at least partially adapted liner after connecting the uncrosslinked filling compound to the prefabricated liner.

22. The method as claimed in claim 14, further comprising applying additional uncrosslinked filling compound to the at least partially adapted liner and connecting the additional uncrosslinked filling compound to the at least partially adapted liner.

* * * * *